(12) United States Patent
Maschino et al.

(10) Patent No.: US 7,758,947 B2
(45) Date of Patent: Jul. 20, 2010

(54) WEB HAVING APERTURES WITH CONVEX SIDES

(75) Inventors: Andrew D. Maschino, Paris, IL (US); Paul E. Thomas, Terre Haute, IN (US)

(73) Assignee: Tredegar Film Products Corporation, Richmond, VA (US)

( * ) Notice: Subject to any disclaimer, the term of this patent is extended or adjusted under 35 U.S.C. 154(b) by 486 days.

(21) Appl. No.: 11/567,346

(22) Filed: Dec. 6, 2006

(65) Prior Publication Data

US 2008/0138574 A1    Jun. 12, 2008

(51) Int. Cl.
*B32B 3/24* (2006.01)
*A61F 13/512* (2006.01)

(52) U.S. Cl. .................. 428/132; 428/131; 604/378; 604/383; 604/385.01; 604/358

(58) Field of Classification Search ................. 428/132, 428/131; 604/378, 383, 385.01, 358
See application file for complete search history.

(56) References Cited

U.S. PATENT DOCUMENTS

| | | | |
|---|---|---|---|
| 3,929,135 A | 12/1975 | Thompson | |
| 4,342,314 A | 8/1982 | Radel et al. | |
| 4,634,440 A * | 1/1987 | Widlund et al. | 604/383 |
| 4,637,819 A | 1/1987 | Ouellette et al. | |
| D362,120 S | 9/1995 | Suskind et al. | |
| 5,536,555 A | 7/1996 | Zelazoski et al. | |
| 5,648,142 A * | 7/1997 | Phillips | 428/132 |
| 5,998,696 A | 12/1999 | Schone | |
| 6,262,331 B1 | 7/2001 | Nakahata et al. | |
| 2005/0003152 A1 | 1/2005 | Thomas et al. | |

FOREIGN PATENT DOCUMENTS

| | | |
|---|---|---|
| EP | 1 297 809 A1 | 4/2003 |
| EP | 1 588 828 A1 | 10/2005 |
| GB | 1 219 643 | 1/1971 |
| GB | 2 158 720 A | 11/1985 |
| WO | WO 00/24351 | 5/2000 |

* cited by examiner

*Primary Examiner*—William P Watkins, III
(74) *Attorney, Agent, or Firm*—Joseph A. Tessari

(57) ABSTRACT

An apertured material comprising a web and a plurality of apertures in the web, each aperture having at least two vertices with a convex flap of the web spanning a pair of the vertices.

17 Claims, 4 Drawing Sheets

CD →

CD →

CD →

WEB HAVING APERTURES WITH CONVEX SIDES

FIELD OF INVENTION

This invention relates generally to an apertured web and, more specifically, to an apertured web of an absorbent article, which is used to absorb bodily exudates while being worn by a user.

BACKGROUND OF INVENTION

The use of apertured films in absorbent articles is well known. As used herein, the term "web" refers to any polymeric web, film or sheet, and the term "apertured web" refers to any web having holes or apertures defined therein. Of particular interest herein are three-dimensional apertured webs in which the apertures are defined by one or more sidewalls in the web which extend from a first or fluid-introduction-facing side of the web and protrude from a second or back-facing side of the web. The wall's protrusion toward the second side gives the web depth, also referred to as "loft." For purposes of description herein, the web is given an up and down orientation with the first side facing up and the second side facing down. It should be understood, however, that this is for descriptive purposes only and should not be used to limit the embodiments of this invention to a particular spatial orientation.

Apertured webs are particularly useful in absorbent articles since they tend to be preferential in their fluid permeability. That is, the apertures are essentially recesses on the first side but are protrusions on the second side. Since fluid tends to flow down into the recesses more readily than it can flow up and into protrusions, fluid flows preferentially from the first side to the second side. Additionally, the thickness of the web or "loft" created by the aperture walls tends to keep the first side of the web elevated above the absorbent element of the article and, therefore, further prevents the flow of fluid from the second side to the first side.

Having these characteristics, apertured webs are commonly used in absorbent articles such as diapers and feminine pads to promote the flow of fluid away from the user's skin and toward an absorbent core. The apertured web may be used as a top sheet which is adjacent to the user's skin or as an acquisition distribution layer which is disposed between the top sheet and the absorbent core and promotes the even distribution of fluid across the absorbent core. In both cases, the apertured web facilitates distribution of fluids over the absorbent core and prevents "rewetting," that is, the migration of fluids up from the absorbent core to the user-facing surface of the article. This promotes a drier surface than that of webs which are solely fiber based and have some amount of wicking action.

In addition to minimizing rewetting, apertured webs must have a minimal "strikethrough" time to be effective and avoid undesirable leakage. Strikethrough time, measured in seconds, is the time required for fluid to leave the first side of the apertured web. Strikethrough time is considered a measure of the efficiency of a topsheet in promptly allowing liquid to be absorbed by an absorbent core. Generally, apertured webs are configured to minimize the strikethrough time so that fluid is immediately transmitted to the absorbent core before it has a chance to run off the first side and leak from the article.

Although effective in preventing rewetting, applicants have found that apertured webs in use today could be improved by decreasing strikethrough time, especially for the more viscous exudates, such as menses, since more viscous fluids are less likely to flow down the apertures into the absorbent core beneath. Furthermore, these three-dimensional apertured webs are also not well suited for moving the semi-solid or viscoelastic components in menses, fecal matter, or other fluid substances, from the first side to the second side. Therefore, there is a need for an absorbent article having an apertured layer which not only prevents rewet, but which also facilitates quicker strikethrough, particularly for viscous exudates, and some removal of the viscoelastic components from their surface. The present invention fulfills this need among others.

SUMMARY OF INVENTION

The present invention relates to an absorbent article having an apertured layer that uses the user's own movement to effectively pump exudates to an absorbent layer. More specifically, rather than configuring an absorbent article to absorb fluids in a static state, applicants recognized that the article could be configured instead to exploit the stresses applied to it in the ordinary course of the user's motion. With this in mind, applicants have developed an apertured web in which the user's movement actuates the walls of the apertures in the web to propel the exudates toward the absorbent layer.

To facilitate this actuation, applicants broke away from conventional aperture shapes. Specifically, applicants have observed that most conventional aperture shapes, such as circles, ovals, elongated boat-shapes, and polygons, are defined by straight or concave side walls. Such geometries lack a side wall that is capable of movement independent from the rest of the web. Applicants have developed instead an aperture configuration defined by at least one convex side or wall between a pair of vertices. The portion of the web defined by the convex wall and an imaginary straight line between the vertices forms a flap that can move independently from the rest of the web.

Applicants have discovered that a user's movement can be used to elongate the web and actuate the convex flaps. More specifically, during ordinary use of an absorbent article worn in the crotch are of a user, the user's motion causes the web to periodically elongate and relax such that the vertices periodically separate and return, thereby causing the convex flap between the vertices to move up and down. Without being bound to any particular theory, applicants believe that the up-and-down motion of the convex flap pumps or otherwise moves the fluid through the apertures to facilitate its absorption in the core beneath. This represents a marked improvement over conventional aperture designs in which the walls defining the apertures remain static during use, and impart no motion to the fluid to be absorbed.

In addition to the pumping action afforded by the convex flaps, apertures having convex walls provide significant improvement by lowering strikethrough time yet have an opening large enough to facilitate the passage of large or viscous menses. Specifically, strikethrough time decreases as the ratio of aperture area to aperture perimeter decreases. The desirability of a small area, however, is countered by the need for a passage of sufficient size to allow larger menses components to pass. These apparently countervailing design criteria are met by the aperture configuration of the present invention. The ratio of area to perimeter for an aperture defined by one or more convex walls tends to be low since the convex walls protrude into the aperture. Even when apertures having large areas are used, the wall perimeter increases in kind such that the area to perimeter remains low. Furthermore, as mentioned above, the flaps tend to open during use, thereby further increasing the effective size of this area. The aperture of the present invention therefore provides a large passageway for larger or more viscous menses components, while still exploiting capillary action. Therefore, a web with apertures defined by one or more convex walls transmits semi-solid or viscoelastic components of exudates with good strikethrough time, not only through pumping action, but also through enhanced capillary action.

Yet another benefit of a web having apertures defined by convex walls is the softer edges presented by the convex walls. That is, unlike other high-capillary action designs, such as stars disclosed in Ouellette et al. (U.S. Pat. No. 4,637,819), the convex-walled apertures of the present invention are not pointed in their midsection and thus are relatively smooth or have obtuse angles, and thus present a softer feel against the user's skin.

One aspect of the invention is an apertured material web comprising one or more apertures defined by one or more convex walls. In a preferred embodiment, the apertured material comprises: (a) a web; (b) at least a first plurality of apertures in the web, each aperture of said first plurality being defined by at least a pair of vertices and a convex flap of the web spanning the pair of the vertices.

Another aspect of the invention is an absorbent article comprising a web having apertures defined by one or more convex walls. In a preferred embodiment, the absorbent article comprises: (a) an aperture web comprising at least a web and at least a first plurality of apertures in the web, each aperture of said first plurality being defined by at least a pair of vertices and a convex flap of the web spanning the pair of the vertices; and (b) an absorbent layer below the apertured web. Preferably, the absorbent article is configured to fit in the crotch area of the user.

Yet another aspect of the present invention is a method of using a user-worn absorbent article comprising an apertured web having apertures defined by convex walls. In a preferred embodiment, the method comprises: (a) positioning the absorbent article described above in the crotch area of a user between the user's legs; and (b) periodically stretching and relaxing the article by moving the legs, the periodic stretching and relaxing causing the pair of vertices to periodically separate and return, thereby causing their respective convex flap to move up and down to move exudates away from the user into the absorbent layer.

DETAILED DESCRIPTION OF PREFERRED EMBODIMENTS OF INVENTION

Figure 1:
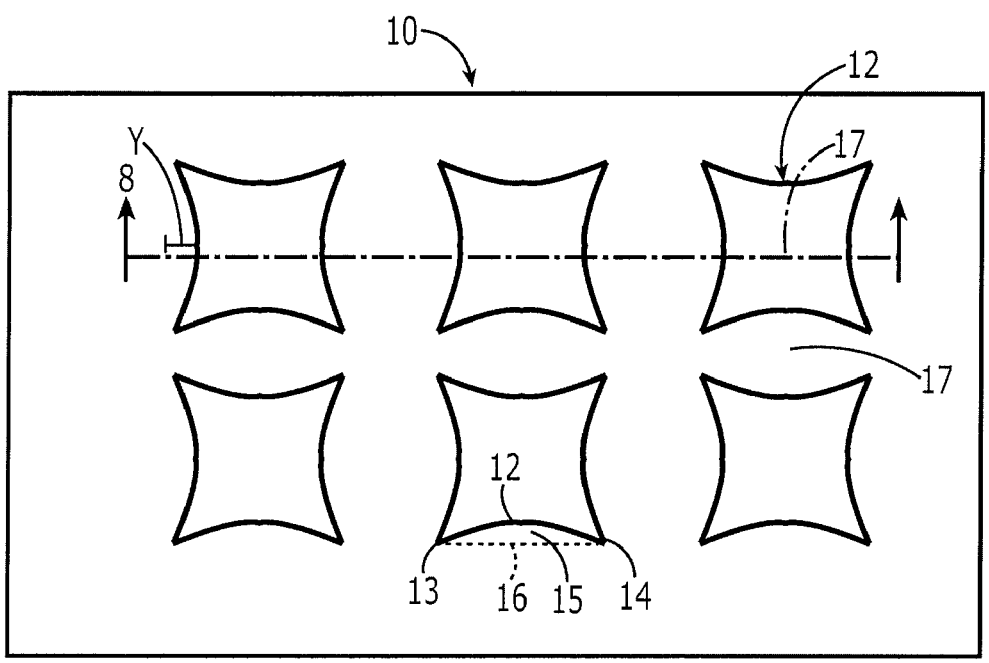
FIG. 1 is a plan view of a web having apertures defined by four convex walls.

Referring to FIG. 1, a preferred embodiment of the web 10 of the present invention is shown. The web 10 comprises a plurality of apertures 11, each aperture 11 defined by at least a pair of vertices 13, 14 across which spans a convex wall 12 of the web to define one side of the aperture 11. This geometry provides for a convex flap 15 adjacent to each aperture. The convex flap 15 is the portion of the web adjacent the aperture 11 which is capable of movement independent of the rest of the web 10. Its area is defined generally by the imaginary straight line 16 between its respective vertices 13, 14 and the convex wall 12.

As used herein, the term "vertex" means a point (as of an angle, polygon, polyhedron, or other shape) that terminates a line or curve or comprises the intersection of two or more lines or curves. The term "convex wall" as used herein means an edge of the web between a pair of vertices that protrudes inwardly into the aperture. It should be understood that the term convex refers to the portion of web that defines the aperture and not to the shape of the aperture itself. Indeed, a convex wall will define a concave aperture.

Figure 8:
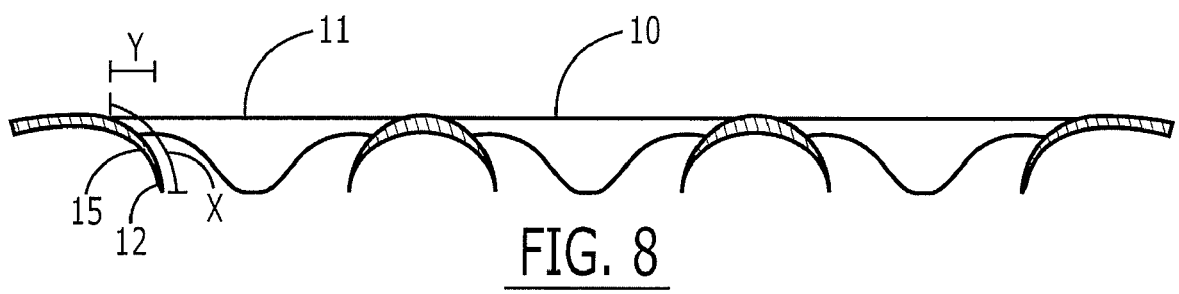
FIG. 8 is a cross sectional view of the web of FIG. 1.

It should also be understood that, unless otherwise stated, all physical characteristics of the web, side walls, apertures, and convex flaps (e.g., shape, area, perimeter, size) are based on a two-dimensional (plan) view of the web from the first side when the web is in a relaxed state. The three-dimensional aspects of the web, apertures, side walls, and flaps are ignored. For example, referring to FIG. 8, a cross section of the web shown in FIG. 1 is shown. Although the convex flap may have a length of x along its surface, when viewed from the first side, it appears to have a length of only y (see FIG. 1). Therefore, for calculation and descriptive purposes herein, the convex flap would be treated as having a length of y.

As mentioned above, the convex flap 15 provides for a number of important benefits over traditional aperture wall shapes. First, the flap 15 can move independently from the rest of the web 10, and perhaps, more importantly, moves as the result of the web being elongated in the direction in which the vertices are aligned. More specifically, as the web is stretched in this direction, pairs of vertices separate causing their respective convex flap to move downwardly relative to the plane of the first side.

Applicants have discovered that the stress applied across absorbent articles during use can be used to actuate the convex flaps 15 adjacent the apertures 11. Specifically, in W/O 2005/0003152 (commonly assigned with present application and incorporated herein by reference), it was recognized that the stress applied to an absorbent article position between the legs of a user is usually from leg to leg. In other words, the stress applied to the article is normal to the direction the user is facing. By aligning the vertices of a convex flap along the axis of stress, i.e., in the direction from leg to leg, applicants have found that the user's own motion, i.e., walking or crawling, can be used to elongate the web and cause the convex flaps to move downwardly with respect to the relaxed plane of the first side. When the force is relieved, the flap moves upwardly and returns to its initial position. This motion can pump or otherwise confiscate viscous fluid matter and pull it into and/or through the aperture, essentially removing it from the first side.

In addition to the confiscating motion offered by the convex flaps, applicants recognize that the aperture's capillary action is also enhanced due to the convex walls. Specifically, the prior art recognizes that capillary action is a function of the area of the opening to the perimeter of the side walls. As this ratio goes down, capillary action increases. For noncircular apertures, this ratio has been described in terms of the Equivalent Hydraulic Diameter (EHD) (see, e.g., Mullane, U.S. Pat. No. 4,324,246), which is expressed as follows:

$$EHD = 4A/P$$

where A is the area of the aperture and P is its perimeter. These parameters may be measured using known techniques such as with an Ames Micrometer as manufactured by the Ames Corporation of Waltham, Mass. For the purposes of showing the change in the ratio of area and perimeter, this EHD formula is a useful tool. Furthermore, this formula thus provides a standardized measurement of aperture size regardless of shape. According to the teaching of Mullane, '246, when this number is below 0.025 inches, capillary action tends to be the dominate mechanisms by which fluids pass through the aperture. Conversely, when this number is above 0.025 inches, capillary action tends to be insignificant and the dominant fluid flow driver is gravity.

Figure 6:
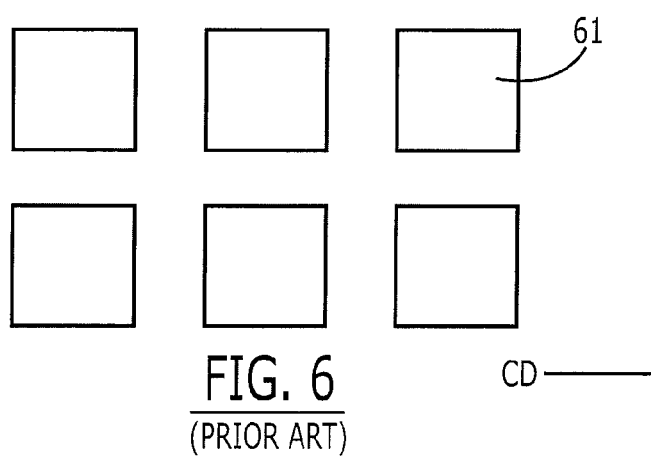
FIG. 6 is a prior art four-sided aperture configuration.

As mentioned above, an aperture comprising convex walls has a low EHD number, but not at the expense of an aperture that is so small that it blocks larger menses components from passing. For example, in Table 1 below, the EHD of the prior art square aperture shown in FIG. 6 is compared to the square aperture having convex walls as shown in FIG. 1.

TABLE 1

| Cell Dimension | Value | |
| --- | --- | --- |
|  | Straight | Convex |
| Area of Individual Cell | 2.55 mm$^2$ | 2.55 mm$^2$ |
| Perimeter of Cell | 5.95 mm | 6.95 mm |
| EHD = 4 (A/P) | 1.72 mm | 1.47 mm |
| EHD in Inches | 0.068 in. | 0.058 in. |
| Screen Open Area | 62.30% | 46.60% |

Here, the prior art square aperture and the square aperture with convex walls have the same area. However, the EHD is significantly less for the aperture of the present invention. Indeed, it has an EHD that is approximately 15% less, which demonstrates a significant change in the ratio of area and perimeter.

It is generally desirable to keep the ratio, as indicated by EHD, as low as possible. This can be done by increasing the curvature of the convex flap. Accordingly, the convex-walled apertures of the present invention have an EHD of no greater than preferably about 0.07 in., more preferably about 0.05 in., and even more preferably about 0.03 in. As a practical limit, however, the curvature of the convex flap is limited by the aperture shape of the forming screen and the ability to form film through it.

Applicants also recognize that the convex walls 15 of the apertured web of the present invention are blunt, not pointy. Thus, they tend to have a softer feel than other low EHD geometries such as stars.

Many different aperture configurations having convex walls are within the scope of the invention. For example, as shown in FIG. 1, the first side of the web 10 defines a pattern of four-sided apertures 11 between lands 17. Each four-sided aperture comprises four convex walls 12 which protrude downward from the first side beyond the second side to their apex. Generally, but not necessarily, the four-sided shape of the aperture will continue downward along the aperture walls for at least a portion of the three-dimensional depth of the aperture. It is not essential that the geometry is fully continuous from the first side to the end of the walls. The perimeter of the aperture will typically change, usually becoming fairly rounded at the apex of the walls.

Figure 2:
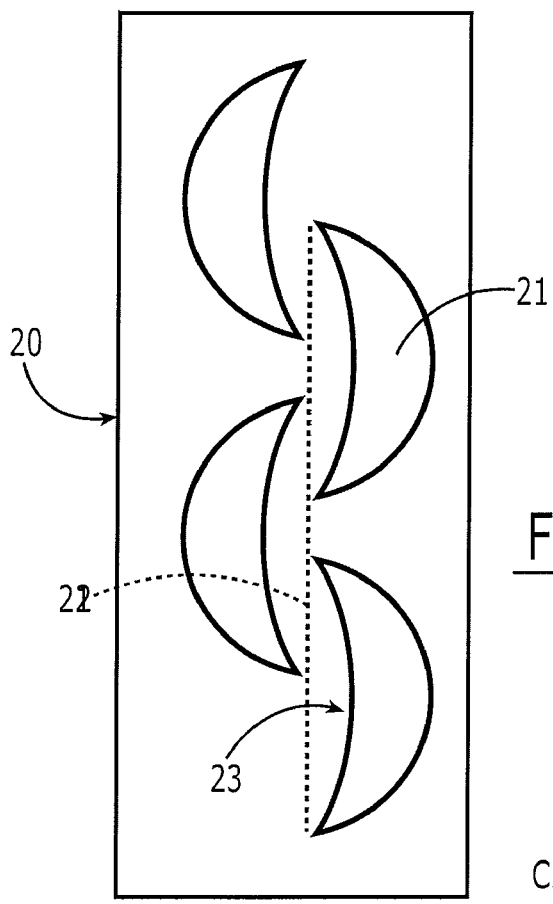
FIG. 2 is a plan view of a web having elongated apertures each with one convex side.

Referring to FIG. 2, another preferred embodiment of the web 20 of the present invention is shown. Web 20 is depicted in a plan view with apertures having one convex wall 23. As with the embodiment show in FIG. 1, the apertures 21 exist between lands 22 and protrude downward from the first side. Ideally, the vertices are aligned normal to the axis whereupon bodily motions will induce the stress to the web. When the resulting flap is pulled and release by the natural stresses applied, it will move up and down.

In addition to the embodiments shown in FIGS. 1 and 2, many other aperture designs are possible, including, for example, a triangular aperture having three convex sides and apertures having one or more convex walls in combination with straight or concave walls. Furthermore, while the fullest benefit of this invention is realized when all the apertures have at least one convex side, there may be instances where, for the sake of functionality, tactile feel, or aesthetic appeal, the apertures may be co-mingled with other apertures of standard geometric specifications. Zones or regions comprising the apertures of this invention may also be incorporated with zones or regions of standard apertures. One skilled in the art of constructing an absorptive device will understand the best combination and varieties of designs or patterns that can be incorporated while using these inventive apertures.

Figure 3A:
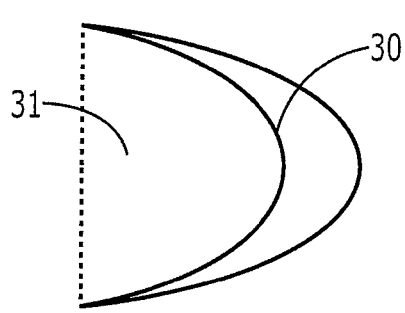
FIGS. 3a-3c show alternative aperture shapes
Figure 3B:
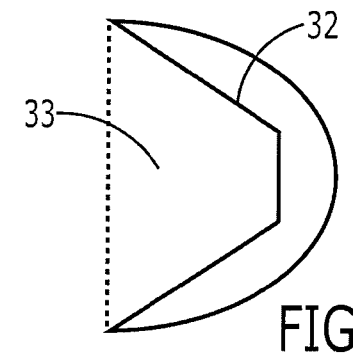

Although the convex walls 12, 23 shown in FIGS. 1 and 2 are curved at a constant radius to connect their respective vertices, this is not necessarily. That is, the scope of the invention includes convex walls that are not only a constant radius curve, but also a non-radius curve or even a rectilinear shape. Indeed, the shape and size of the convex flap 15 can be optimized for a particular application. For example, it may be preferable to form larger flaps for imparting a greater pumping action to particularly viscous exudates. Referring to FIG. 3a, a convex wall 30 having a hyperbolic profile is shown. Such a configuration may be preferred in certain applications since it forms a flap 31 that has a greater area than one defined by a constant radius convex wall. In yet another embodiment, the convex wall 32 may be defined by a series of relatively short straight lines, which, overall, create a convex shape as shown in FIG. 3b. The convex wall 32 and the imaginary line between the two vertices define a trapezoidal convex flap 33. As with flap 31, flap 32 has more area than one defined by a constant radius convex wall.

Figure 3C:
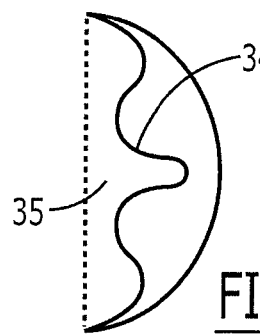

Among other factors to consider in sizing the convex flap is the resulting size of the aperture. To reduce strikethrough time, it is helpful if the ratio of the aperture's area to its perimeter is kept as low as is practical. Therefore, the size and shape of the convex flap and the area of the aperture ought to be considered together. In this regard, FIG. 3c shows a convex wall 34 having an undulating curve in which only a portion of the wall is convex. Such a configuration may be preferred for enhancing capillary action since it increases aperture perimeter relative to aperture size.

The web of the present invention is formed from conventional materials using conventional fabrication techniques. For example, the web may comprise a traditional polyolefin such as polyethylene or polypropylene, which is extruded as a sheet and vacuum formed as disclosed, for example, in U.S. Pat. No. 4,456,570. Alternatively, the web may be a nonwoven material formed using traditional techniques such as melt blown, spun bonded, airlaid, hydroentangled or other methods, and apertured using traditional techniques such as hot needles of certain shapes or intermeshing perforating rollers, also of certain shape and configuration which will render the desired aperture. The web of the present invention may also be combined with other apertured webs and nonwoven webs to create composite laminations. Again, such lamination techniques are well known and will not be addressed in detail herein.

Preferably, the web comprises an inelastic material which is unable to absorb elastically the stress applied across it such that the energy will be directed to separating the vertices and actuating the convex flaps as described above. In other words, it is preferable for the web to elongate as a function of the vertices being separated and the apertures deforming rather than the material absorbing the stress.

The web of the present invention is well suited for any application involving the distribution of fluid from a user-facing surface to an absorbent layer beneath the surface. It is particularly well suited for absorbent articles worn by a user in the crotch area. Such absorbent articles include, for example, baby diapers, adult diapers or incontinence inserts, pull-up disposable pants, feminine napkins, and panty liners. Generally, such articles have a portion which is slender enough to fit between the user's legs. Often, such articles are hour glass-shaped to provide a contoured fit around the user's legs. Such configurations are well known. It should be understood, however, that the invention is not limited to these applications and may also be used in other absorbent articles such as bed pads, baby wipes, bibs, spill pads, household wipes, industrial wipes and the like.

Absorptive articles typically comprise a topsheet which is adjacent to the wearer, an absorbent layer beneath the top sheet for absorbing the fluid exuded from the user, and often a fluid-impervious backsheet disposed on the side of the absorbent layer opposite the top sheet to prevent leakage. An absorbent article may also be constructed with an intermediate fluid transmitting layer between the topsheet and the core. Such intermediate layers are known for distributing the fluid in a more controlled fashion across the absorbent layer to promote even absorption. Generally, these layers are arranged to allow gravity to pull the fluid through the top sheet and into the absorbent layer. The web of the present invention can be used as either the topsheet or as the intermediate layer.

In use, fluid is introduced by the wearer on the first side. Regardless of whether the material of this invention is used as the topsheet or intermediate layer, it transmits the fluid through itself and into absorbent core. Applicants believe that the actuation of the convex flaps, during the user's ordinary movement, helps to move or confiscate highly viscous or semi-viscous, clot-like or gel-like matter, such as that which exists in menstrual fluid or fecal matter, from the first side of the apertured formed web to the absorbent core. It has been shown that incorporating convex sides to the perimeter of the aperture increases the strikethrough time of a higher viscosity fluid by about 45%.

EXAMPLES

Example 1

Strikethrough Time

This example demonstrates the enhanced strikethrough time of the web of the present invention for viscous fluids compared to prior art aperture designs. An apertured web having the configuration shown in FIG. 2 was tested using a fluid with a relatively high viscosity. Traditionally, a solution of two parts Pepto-Bismol® and one part distilled water is used as an Artificial Menses Fluid (AMF) to determine strikethrough time and rewet for top sheet materials used in feminine sanitary napkins. For this test, a more viscous solution was desired in an attempt to represent the higher viscosity components of either menses or fecal matter. Specifically, pure Pepto-Bismol®, without any dilution, was used to render a Higher Viscosity Artificial Menses Fluid (HVAMF). It has a viscosity of 20.2 s (as measured by Viscosity Cup Method in accordance with ASTM D-4212, 44 ml Cup size), which is significantly more than the viscosity of 14.3 s for the typical AMF test fluid (2:1 diluted Pepto-Bismol®).

The web of the present invention comprises an extruded polyethylene blend having vacuum formed apertures as shown in FIG. 2 and prepared generally in accordance with U.S. Pat. No. 4,456,570.

Table 2 below shows a strikethrough time of the web of the present invention to be about 30 seconds faster than that of the standard web.

TABLE 2

| Geometry | HVAMF, sec. |
|---|---|
| Convex | 31 |
| Convex | 39 |
| Convex | 41 |
| Avg. | 37 |
| Standard | 68 |
| Standard | 63 |
| Standard | 70 |
| Avg. | 67 |

Comparative Example

Flap Actuation

This example demonstrates that the walls of prior art apertures do not move significantly, when the web is stressed. The prior art apertured web in this example was prepared in the same way as Example 1, but has a five-sided aperture 71 as shown in FIG. 7.

Figure 4A:
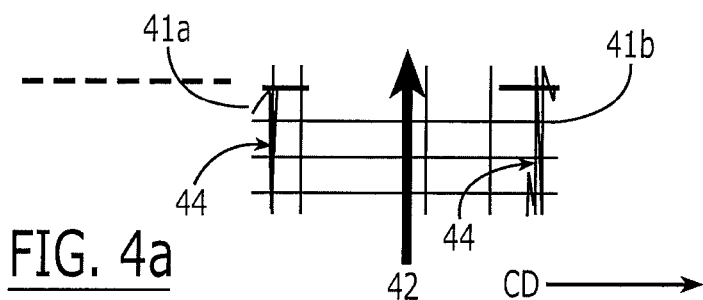
FIG. 4 is the comparative laser scanned profile graphic of the second side of the common prior art aperture of FIG. 2 in the relaxed and stretched phase.
Figure 7:
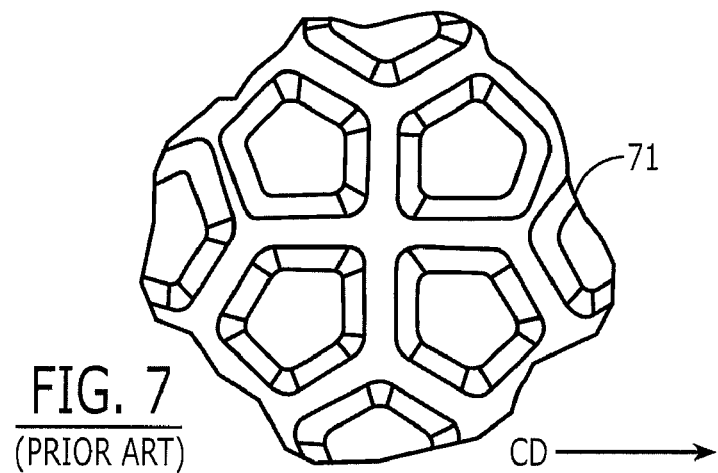
FIG. 7 is a prior art five-sided aperture configuration.

Referring to FIG. 4a, a profile graph is shown of an inverted second side (pointing upward in this profile data from the laser scan, yet normally pointing downward in an absorbent device) of an aperture of FIG. 7. Inverted aperture 40r has sidewalls 41a and 41b bordering aperture 42 and culminating at their apex on second side plane 43. As depicted by laser scanned profile lines 44, the second side positions of the sidewalls are virtually in the common plane of the second side while in the relaxed phase.

Figure 4B:
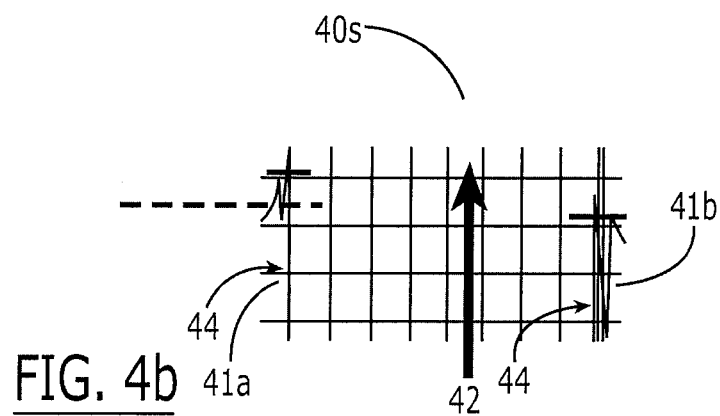

The stress applied to the web to stretch it was such that it elongated to a width of 20-25% greater in the Cross Direction (CD) than its relaxed width. As is well known in the art, the CD is the direction, which, in an absorptive device, is the side to side, or leg to leg, versus front to back, direction. FIG. 4b shows the stretched profile graph of the inverted second side of the aperture of FIG. 7. Inverted aperture 40s has sidewalls 41a and 41b, bordering aperture 42 and culminating at their apex on second side plane 43. As depicted by laser scanned profile lines 44, the second side positions of the sidewalls 41a and 41b have only shifted slightly. This motion is essentially insignificant and is not enough to create any confiscating action.

Example 2

Flap Actuation

Figure 5A:
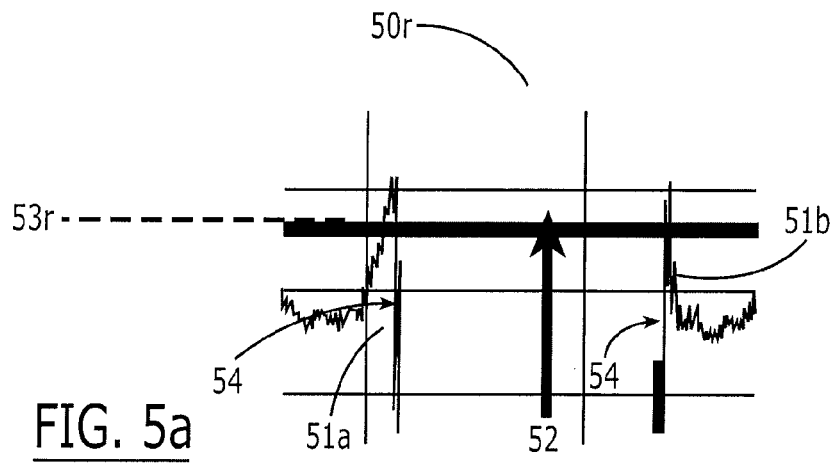
FIG. 5 is the comparative laser scanned profile graphic of the second side of the inventive aperture of FIG. 2 in the relaxed and stretched phase.

This example demonstrates movement of the convex flaps of the present invention relative to the standard web in the Comparative Example. FIG. 5a shows the relaxed profile graph of the inverted second side of the web of the present invention described above with respect to Example 1. Inverted aperture 50r has sidewalls 51a and 51b bordering aperture 52 and culminating at their apex on second side plane 53r. As depicted by laser scanned profile lines 54, the second side positions of the sidewalls are virtually in the common plane 53r of the second side while in the relaxed phase of profile 50r.

Figure 5B:
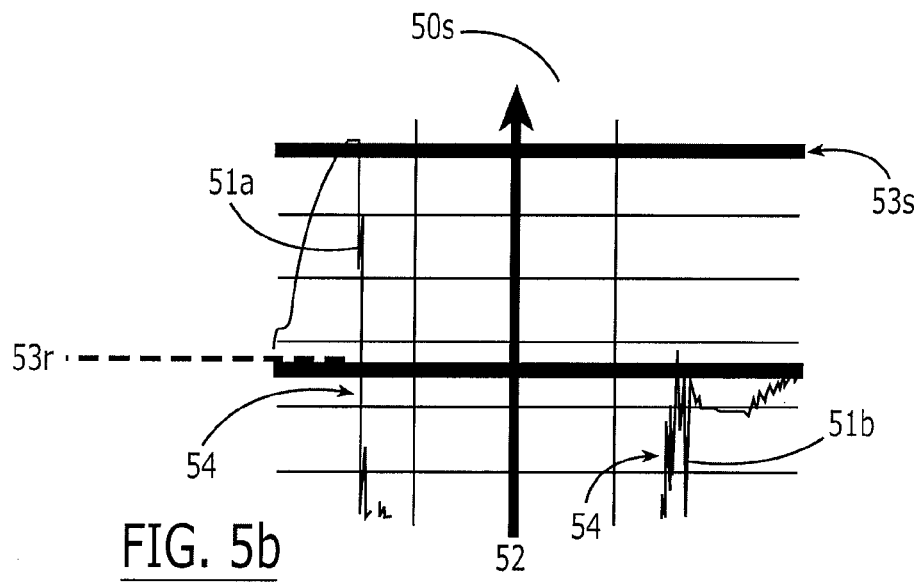

The stress applied to the web to stretch it was such that it elongated to a width of 20-25% greater in the Cross Direction (CD) than its relaxed width. FIG. 5b shows a profile graph 50s of the inverted second side of web of the present invention. Inverted aperture 5s has sidewalls 51a and 51b bordering aperture 52 and culminating at their apex on second side. As depicted by laser scanned profile lines 54, the second side positions of the sidewalls 51a and 51b are now in significantly different positions. Sidewall 51a is in a considerably lower plane 53s, while sidewall 51b has essentially remained in the original plane 53r. This downward motion is significant enough to move viscous matter off the first side.

What is claimed is:

1. A three-dimensional apertured web having a first plurality of apertures, each aperture being defined by sidewalls that originate on a first surface of the web and depend therefrom and terminate in an apex beyond a second surface of the web, each aperture further having at least a pair of vertices and a convex flap of said web spanning said pair of vertices, said convex flap forming at least one of said sidewalls and being movable in an up and down motion in response to stress applied normal to an axis defined a respective said pair of vertices and independent from the remainder of the web.

2. The three-dimensional apertured web of claim 1, wherein each aperture comprises three or more vertices with a convex flap between each pair of said vertices.

3. The three-dimensional apertured web of claim 1, wherein each aperture comprises four vertices with four convex flaps between said vertices.

4. The three-dimensional apertured web of claim 1, wherein the convex flap is defined by a convex wall that curves away from a plane of the web.

5. The three-dimensional apertured web of claim 1, wherein said vertices are aligned in a machine direction.

6. The three-dimensional apertured web of claim 1, wherein said web is nonelastic.

7. The three-dimensional apertured web of claim 1, wherein said web is an extruded web.

8. The three-dimensional apertured web of claim 1, wherein said web is a nonwoven.

9. The three-dimensional apertured web of claim 1, wherein said web comprises bonded or unbonded fibers.

10. The three-dimensional apertured web of claim 1, further comprising a second plurality of apertures which are not defined by one or more convex walls.

11. An absorbent article comprising:
a three-dimensional aperture web comprising a first plurality of apertures, each aperture being defined by sidewalls that originate on a first surface of the web and depend therefrom and terminate in an apex beyond a second surface of the web, each aperture further having at least a pair of vertices with a convex flap of said web spanning said pair of vertices, said convex flap forming at least one of said sidewalls and being movable in an up and down motion in response to stress applied normal to an axis defined a respective said pair of vertices and independent from the remainder of the web; and
an absorbent layer below said three-dimensional apertured web.

12. The absorbent article of claim 11 wherein said article is configured to fit between the legs of a user.

13. The absorbent article of claim 11, further comprising a nonwoven layer bonded to said first surface of said three-dimensional apertured web.

14. A user-worn absorbent article comprising the absorbent article of claim 12.

15. A method of using a user-worn absorbent article, said article comprising a three-dimensional aperture web comprising a first plurality of apertures, each aperture being defined by sidewalls that originate on a first surface of the web and depend therefrom and terminate in an apex beyond a second surface of the web, each aperture further having at least a pair of vertices with a convex flap of said web spanning said pair of vertices, said convex flap forming at least one of said sidewalls and being movable in an up and down motion in response to stress applied normal to an axis defined a respective said pair of vertices and independent from the remainder of the web and an absorbent layer below said web, said method comprising:
positioning said article in the crotch area of a user between the user's legs; and
periodically stretching and relaxing said article through the movement of said legs, said periodic stretching and relaxing causing said pair of vertices to periodically separate and return, thereby causing said convex flap to move up and down to move exudates away from said user and into said absorbent layer.

16. The method of claim 15, wherein said periodic stretching and relaxing of said article results from moving the legs forward and backward during walking or crawling.

17. The method of claim 15, wherein said fluid has a viscosity of greater than 14.2 s.

* * * * *